United States Patent
El-Demerdash et al.

(12)

(10) Patent No.: US 6,751,688 B1
(45) Date of Patent: Jun. 15, 2004

(54) METHOD AND APPARATUS FOR SAFE CT SCANNER BUTTON PRESSES

(75) Inventors: Mohamed El-Demerdash, Milwaukee, WI (US); David Pitterle, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/506,106

(22) Filed: Feb. 17, 2000

(51) Int. Cl.[7] ............................................... G06F 13/14
(52) U.S. Cl. ........................ 710/67; 710/73; 710/106; 340/310.01; 378/117
(58) Field of Search ........................ 710/67, 73, 106; 340/310.01; 378/117

(56) References Cited

U.S. PATENT DOCUMENTS

| | | | | |
|---|---|---|---|---|
| 4,991,193 A | * | 2/1991 | Cecil et al. | 378/117 |
| 5,920,253 A | * | 7/1999 | Laine | 340/310.01 |
| 6,031,535 A | * | 2/2000 | Barton | 345/840 |

OTHER PUBLICATIONS

"Bosch Controller Area Network (CAN) Version 2.0 Protocol Standard," Motorola, 1998, pp. 8–1 to 8–2 and 9–1 and 9–8 (entire document is available in Adobe PDF format at http://mot–sps.com/mcu/documentation/pdf/bcanv2r3.pdf).

* cited by examiner

Primary Examiner—Jeffrey Gaffin
Assistant Examiner—Mohammad O. Farooq
(74) Attorney, Agent, or Firm—Carl B. Horton, Esq.; Armstrong Teasdale LLP

(57) ABSTRACT

The present invention is, in one embodiment, a method for efficiently and reliably communicating button presses electronically on a network from one or more push button nodes each having at least one push button, to a master node. This method includes steps of: generating status messages indicative of a push button states at each of push button node; communicating the status messages to the master node via the network; determining, at the master node, the state of the push buttons at each of the push button nodes from the communicated status messages; and triggering a response of the master node, in accordance with the statuses of the push buttons determined from the communicated status messages.

30 Claims, 3 Drawing Sheets

METHOD AND APPARATUS FOR SAFE CT SCANNER BUTTON PRESSES

BACKGROUND OF THE INVENTION

This inventions relates to methods and apparatus for interfacing a device to a set of push button inputs, and more particularly to methods and apparatus for interfacing a CT scanner to a network to create a safe and efficient user interface for accepting push button inputs.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Additional operator inputs to CT systems have been provided as CT systems become more and more flexible. The provision of additional push buttons on the gantry of the CT system to accommodate new functions has resulted in an increased number of cables. Although hard-wired connections to push buttons provide both speed and safety in operation, increased cabling requirements pose additional construction and material costs. In addition, cable routing problems occur due to the size of the required cables.

It would therefore be desirable to provide methods and apparatus to accommodate the need for additional push buttons on CT scanning systems without requiring large, costly cables, without compromising the safety and speed of a hard-wired connection.

BRIEF SUMMARY OF THE INVENTION

There is therefore provided, in one embodiment, a method for efficiently and reliably communicating button presses electronically on a network from one or more push button nodes each having at least one push button, to a master node. This method includes steps of: generating status messages indicative of a push button states at each of push button node; communicating the status messages to the master node via the network; determining, at the master node, the state of the push buttons at each of the push button nodes from the communicated status messages; and triggering a response of the master node, in accordance with the statuses of the push buttons determined from the communicated status messages.

The above described method accommodates the need for additional push buttons on CT scanning systems without requiring large, costly cables, without compromising the safety and speed of a hard-wired connection.

DETAILED DESCRIPTION OF THE INVENTION

Figure 1:
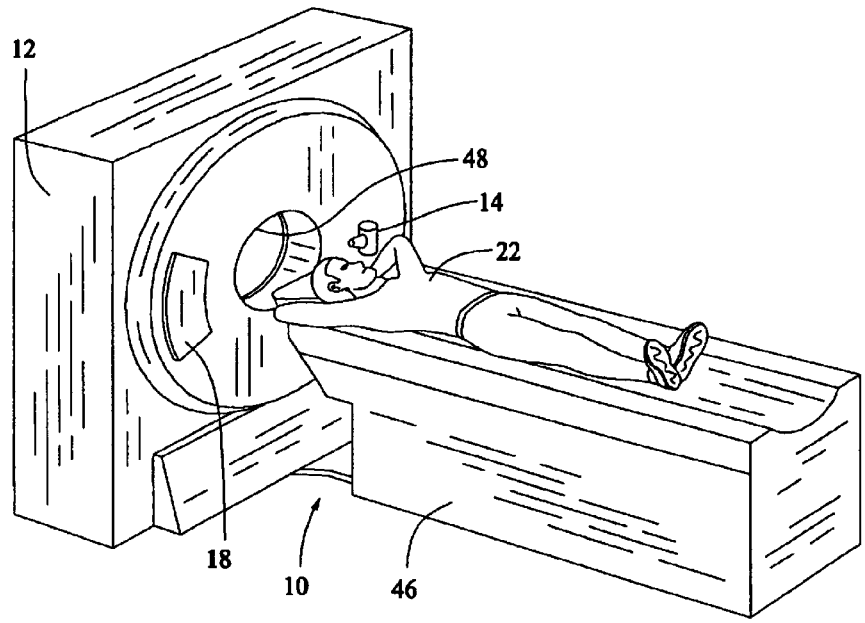
FIG. 1 is a pictorial view of a CT imaging system.
Figure 2:
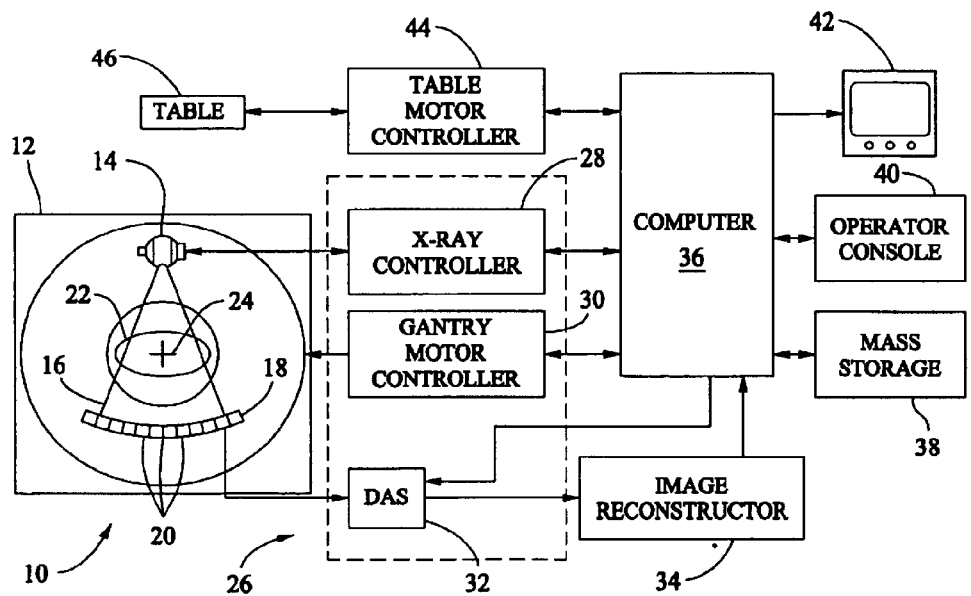
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
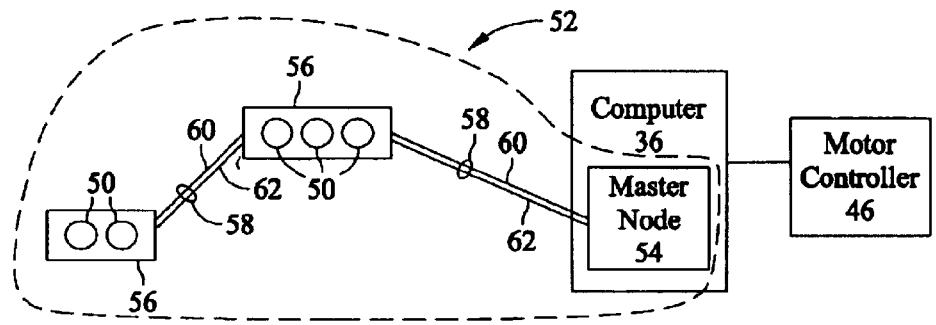
FIG. 3 is a block schematic diagram of one embodiment of a system for detecting and responding to push button presses.

In one embodiment and referring to FIG. 3, computer 36 is responsive to button presses of push buttons 50 to control table motor controller 46, for example, among other things. When a button is pressed, a message is output over a controller area network (CAN) 52. CAN 52 includes a master node 54, which is incorporated in the hardware and software of computer 36 in one embodiment, or in a separate unit in another embodiment. For flexibility, CAN 52 also includes as many push button nodes 56 as required by an application such as CT scanner or imaging system 10. (Push button nodes 56, in one embodiment, include push buttons 50 mounted on gantry 12 of CT imaging system 10.) Master node 54 is responsive to push buttons to detect any valid pressed button 50 in network 52. Master node 54 also, on a periodic basis, outputs a status message of buttons 50 (to computer 36 in this embodiment), thus mirroring an output of a corresponding hard-wired implementation. Master node 54 also senses faults in CAN 52 such as a faulty push button node 56.

In one embodiment, push button node 56 initiates communication of messages to master node 54 on a periodic basis over CAN 52, which comprises a high speed-serial bus 58, also referred to as Controller Area Network Bus. In one embodiment, these messages are sent over a period that is half of the time specified for master node 54 to be informed of a button 50 press. When a button 50 is pressed, the message includes an indication of, the button press. Because of the timed, repetitive messages sent by push button node 56, each button 50 press that occurs will be reported to master node 54 in a time less than that specified for master node 54 to be informed of a button press. In still other embodiments, messages are sent sufficiently often by push button node 56 so that, no matter when a button 50 press .occurs, master node 54 receives a message from the affected push button node 56 in sufficient time to ensure an appropriate system response. In these embodiments, a "sufficient time to respond" depends, for example, on the "appropriate system response." An "appropriate system response" depends, for example, on the functions that the various buttons 50 operate and control. Master node 54 determines the state of each push button 50 from the communicated status messages, and triggers a response of the master node in accordance with the statuses determined from the communicated status messages. This response is a further communication of push button states to computer 36 in this embodiment. In other embodiments, master node 54 provides I/O ports that mimic or mirror push button states. In one embodiment, each I/O port corresponds to a different push button 50.

Master node 54 checks all push button nodes 56 to ensure that the expected periodic messages from each push button node 56 are received. Each push button node 56 is allotted a pre-determined number of wake-up cycles (i.e., a wake-up cycle of master node 54 during which it outputs a status of buttons 50, for example, via I/O ports) without changing the last button status sent by that push button node 56. Master node 54 "defaults" the status of that push button node 56 to a known safe state by triggering a response corresponding to the known safe state. The allowance of an extra missed wake-up cycle helps to create a "jitter-free" system. The setting of the status of a push button node 56 also helps guard against stuck buttons 50. As a further safety measure, in one embodiment, each CAN 52 packet containing push button 50 status also contains a checksum value generated by the push button node 56. The checksum is used by master node 54 to validate packets from push button nodes 56.

In one embodiment, for further security and safety, each master node 54 and push button node 56 is equipped with a CPU watchdog timer to guard against firmware errors. Also, all buttons 50 are wired so as to be active-high to guard against unintentional grounding, such as that which may cause a stuck button 50 indication. Also in one embodiment, each monitored button 50 in a push button node 56 creates two signals, one unique to that particular pressed push button 50, and another logically ORed with all other push buttons 50 of that push button node 56. The logically ORed output and the unique output signal are read by push button node 56, which performs a redundancy check using these signals for any pressed button 50. If an inconsistency is encountered, push button node 56 communicates an error indication to master node 54.

Figure 4:
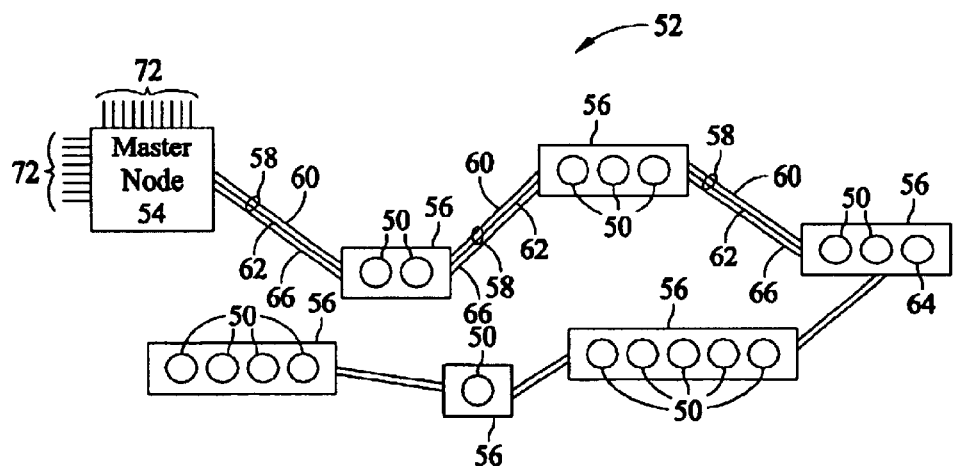
FIG. 4 is a block schematic diagram of another, series-connected embodiment, showing a separate circuit for a critical button.
Figure 5:
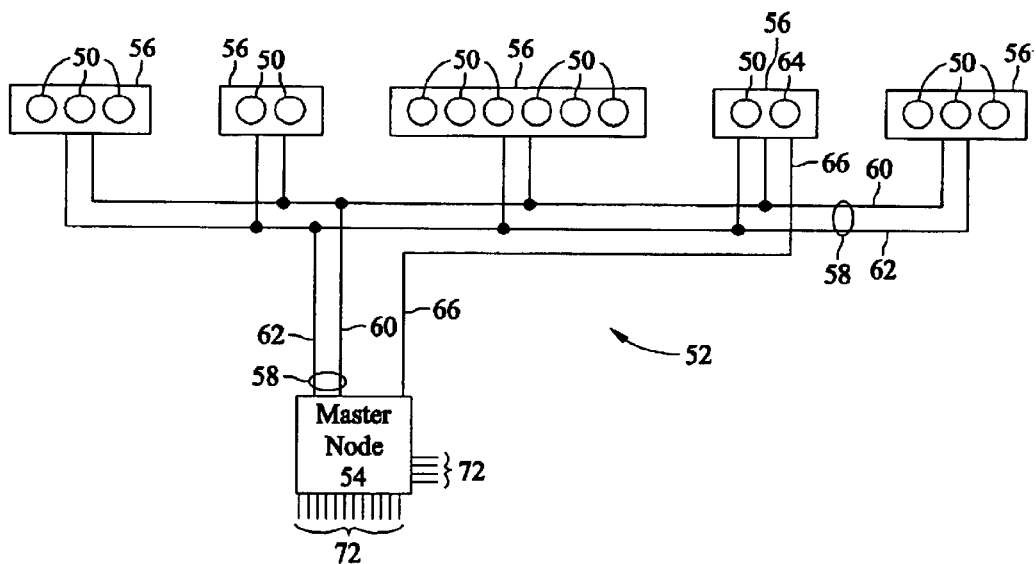
FIG. 5 is a block schematic diagram of a parallel-connected embodiment, also showing a separate circuit for a critical button.
Figure 6:
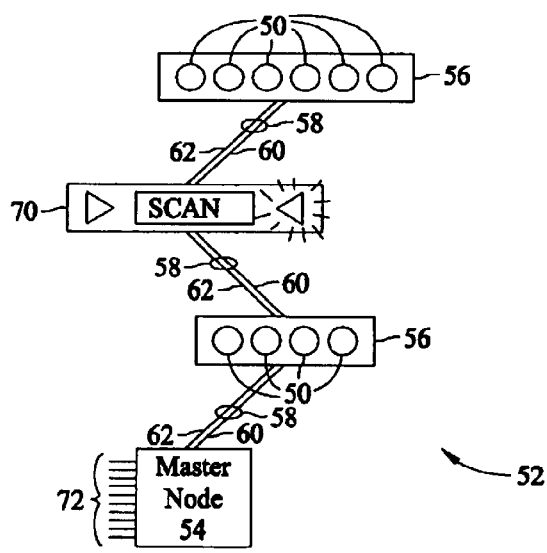
FIG. 6 is a block schematic diagram of another embodiment in which a display node is present.

Push button nodes 56 are connected to master node 54 by a series connection in one embodiment, as exemplified by the diagram of FIG. 4, and by a parallel connection in another, as exemplified by the diagram of FIG. 5. (Although not illustrated, combinations of serial and parallel connections are used in some embodiments. For example, in one embodiment, one of push button nodes 54 in FIG. 5 is replaced by a series connection of push button nodes 54.) Parallel or series bus 58 include at least a CAN high wire 60 and a CAN low wire 62. Thus, only two conductors are needed for bus 58 for communicating status messages from push button nodes 54 to master node 56. However, in at least one embodiment, one or more "critical" buttons 64 are provided that control features of scanning device 10 requiring immediate action. A separate, hard-wired circuit 66 is provided for each critical button 64. Each hard-wired circuit 66 needs only one additional conductor, because one bus 58 line (for example, CAN low wire 62) is shared for this purpose in one embodiment. However, in another embodiment, each hard-wired circuit 66 comprises a pair of conductors and does not share any conductors with buttons 50. Depending on a location of a critical button 64, in a series connection such as that exemplified in FIG. 5, a dedicated, hard-wired circuit 68 may pass directly through one or more push button nodes 56 on its way to master node 54. In a parallel connection embodiment such as that represented in FIG. 5, each push button node 56 is directly connected to master node 54, so there is no need for a "pass through" for a dedicated circuit 66. When a critical button 64 is pressed, a signal is immediately communicated to master node 54, separately and independently of status messages concerning push buttons 50. A response of master node 54 is then immediately triggered in response to the immediately communicated signal. The total time from a critical button 64 press to the triggering of the response is thus small or negligible. In any case, this time is less than a period time of the periodic status messages In one embodiment and referring to FIG. 6, CAN 52 is a two-way network having one or more display or indicator nodes 70, each having associated controlling circuitry (not shown) that is addressable by master node 54. Display nodes 70 are responsive to CAN display messages sent by master node 54 for displaying indications, values, alarms, alphanumeric symbols, or types of messages to a user. In one embodiment, for critical messages or indications that are to be displayed, master node 54 selectively includes a checksum with the CAN display message. A displaying push button node 56 includes circuitry for verify the checksum as well as for displaying the message. In one embodiment, each message is sent over CAN 52, a high-speed serial bus configured for sending messages to specific nodes. Each message is provided with a message header identifying its destination and/or source, and master node 54 and/or display nodes 70 are provided with integral ID filters so that, as required, messages are identified as to source and/or destination. Display nodes 70 need not be incorporated into separate units. In one embodiment, displays or indicators and their associated controlling circuitry are built or incorporated into push button nodes 56.

In one embodiment and again referring to FIG. 6, I/O ports 72 are provided to interconnect with a device such as computer 36 of CT imaging system 10. I/O ports 72 are under control of master node 54 and are configured to mimic outputs of a corresponding hard-wired implementation. Exemplary configurations include, but are not limited, to those in which I/O ports 72 are configured to appear as switch closures and/or reduced resistance between contacts, with each I/O port 72 corresponding to a different push button 50.

From the preceding description of various embodiments of the present invention, it is evident that CAN 52 provides a push button detection system with both safety and efficiency. Safety is provided both through redundancy (for example, checksums), watchdog timers, and safe default conditions. Polled modes of operation are avoided to provide a system fast enough to handle time-critical medical applications, as well as other applications requiring push button networks having similar characteristics. Predictability is achieved as a result of assignments of particular time periods in which each push button is to transmit its status. A transmitter time can be dedicated to display nodes (if any), and receiver time dedicated to push button nodes, thereby increasing the efficiency of CAN 52. In one embodiment, master node 54 and CAN 52 are configured so that master node 54 addresses specific push button nodes 56. If and when master node 54 detects an error on one of push button nodes 56, a message is sent to the push button node 56 to signal the error and to cause master node 54 to default to a safe state for the faulty push button node 56 without disturbing the integrity of the remainder of the network. In addition, because nodes are wired in a network, the complexity and size of cables required to accommodate large numbers of buttons is reduced, and routing of cables is simplified.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. The present invention is applicable to many other CT systems, including "fourth generation" systems wherein the detector is a full-ring stationary detector and only the x-ray source rotates with the gantry, and to other applications and devices requiring push button switches. Accordingly, the spirit and scope of the invention are to be limited only by the terms of the appended claims and legal equivalents.

What is claimed is:

1. A method for efficiently and reliably communicating button presses electronically on a serial network from one or more push button nodes each having at least one push button, to a master node, said method comprising the steps of:

generating status messages indicative of a state of the at least one push button at each of the push button nodes when the at least one push button is pressed and generating status messages indicative of a state of the at least One push button at each of the push button nodes when the at least one push button is not pressed;

communicating the status messages to the master node via the network;

determining, at the master node, the state of the push buttons at each of the push button nodes from the communicated status messages; and triggering a response of the master node, in accordance with the statuses of the push buttons determined from the communicated status messages.

2. A method in accordance with claim 1 wherein the status messages are generated periodically at each of the push button nodes.

3. A method in accordance with claim 2 further comprising the step of checking, at the master node, expected status message arrivals from each of the push button nodes; and further wherein the step of triggering a response of the master node comprises the step of defaulting, to a known safe state, status outputs of the master node that corresponding to the push-buttons of a push button node that misses a pre-determined number of wake-up cycles.

4. A method in accordance with claim 2 wherein the master node comprises a plurality of I/O ports corresponding each corresponding to a different one of the push buttons, and wherein triggering a response of the master node, in accordance with the statuses of the push buttons comprises mirroring the statuses via the plurality of I/O ports.

5. A method in accordance with claim 1 wherein the network is a two-wire network comprising a plurality of push-button nodes, and communicating the status messages to the master node via the network comprises communicating the status messages to the master node via the two wires of the network.

6. A method in accordance with claim 1 and further comprising the steps of the master node addressing and communicating a display message to a display node; and the addressed display node producing a display in accordance with the communicated display message.

7. A method in accordance with claim 6 wherein the master node addressing and communicating a display message to a display node comprising the step of the master node selectively generating and including a checksum with critical display messages.

8. A method for efficiently and reliably communicating button presses electronically on a serial network from one or more push button nodes each having at least one push button, to a master node, said method comprising the steps of:

generating status messages indicative of a state of the at least one push button at each of the push button nodes, wherein the status messages are generated periodically at each of the push button nodes;

communicating the status messages to the master node via the network;

determining, at the master node, the state of the push buttons at each of the push button nodes from the communicated status messages;

triggering a response of the master node, in accordance with the statuses of the push buttons determined from the communicated status messages, wherein generating status messages indicative of a state of the at least one push button at each of the push button nodes comprises the step of generating, at each of the push button nodes, a checksum value included in the status message generated at the push button node; and validating the checksum values at the master node to confirm that the master node is receiving valid status messages.

9. A method for efficiently and reliably communicating button presses electronically on a serial network from one or more push button nodes each having at least one push button, to a master node, said method comprising the steps of:

generating status messages indicative of a state of the at least one push button at each of the push button nodes, wherein the status messages are generated periodically at each of the push button nodes;

communicating the status messages to the master node via the network;

determining, at the master node, the state of the push buttons at each of the push button nodes from the communicated status messages;

triggering a response of the master node, in accordance with the statuses of the push buttons determined from the communicated status messages;

generating, when a push button is pressed, a signal unique to the pressed push button and a signal representing a logical combination of states of all of the push buttons of a push button node on which the pressed push button is located; and performing a redundancy check on the pressed push button using the signal representing the logical combination of states, at the push button node on which the pressed push button is located.

10. A method in accordance with claim 9 wherein generating a signal representing a logical combination of states of all of the push buttons of a push button node on which the pressed push button is located comprises logically ORing a signal for the push button being pressed with signals of all of the other buttons of the push button node on which the pressed push button is located.

11. A method for efficiently and reliably communicating button presses electronically on a serial network from one or more push button nodes each having at least one push button, to a master node, wherein the master node is hardwired to a critical button of a push button node, said method comprising the steps of:

generating status messages indicative of a state of the at least one push button at each of the push button nodes, wherein the status messages are generated periodically at each of the push button nodes;

communicating the status messages to the master node via the network;

determining, at the master node, the state of the push buttons at each of the push button nodes from the communicated status messages;

triggering a response of the master node, in accordance with the statuses of the push buttons determined from the communicated status messages;

immediately communicating a signal indicative of the at least one critical button being pressed separately from the generated status messages; and immediately triggering a response of the master node in accordance with the immediately communicated signal;

said immediate communication and said immediate triggering occurring within a time less than a period of the periodically generated status messages.

12. A system for efficiently and reliably communicating button presses electronically, said system comprising a serial network of one or more push button nodes each having at least one push button, and a master node, said system configured to:

generate status messages indicative of a state of the at least one push button at each of the push button nodes when the at least one push button is pressed and generate status messages indicative of a state of the at least one push button at each of the push button nodes when the at least one push button is not pressed;

communicate the status messages to the master node via the wired network;

determine, at the master node, the state of the push buttons at each of the push button nodes from the communicated states messages; and trigger a response of the master node, in accordance with the statuses of the push buttons determined from the communicated status messages.

13. A system in accordance with claim 12 further configured to periodically generate status messages at each of the push button nodes.

14. A system in accordance with claim 13 further configured to check, at the master node, expected status message arrivals from each of the push button nodes; and further wherein being configured to trigger a response of the master node comprises said system being configured to default, to a known safe state, status outputs of the master node that corresponding to the push-buttons of a push button node that misses a pre-determined number of wake-up cycles.

15. A system in accordance with claim 13 wherein the master node comprises a plurality of I/O ports corresponding each corresponding to a different one of the push buttons, and wherein said system being configured to trigger a response of the master node, in accordance with the statuses of the push buttons comprises said system being configured to mirror the statuses via the plurality of I/O ports.

16. A system in accordance with claim 12 wherein the wired network is a serially-connected network.

17. A system in accordance with claim 12 wherein the wired network is a parallel-connected network.

18. A system in accordance with claim 12 and further comprising a watchdog timer at each of the push button nodes and the master node configured to guard against firmware errors.

19. A system in accordance with claim 12 wherein each push button is configured to be active high.

20. A system in accordance with claim 12 further comprising a display, and further wherein the master node is configured to address and communicate a display message to the display; and the addressed display is configured to produce a display in accordance with the communicated display message.

21. A system in accordance with claim 20 wherein the display is incorporated in a push button node.

22. A system in accordance with claim 20 further comprising a display node in which the display is incorporated.

23. A system in accordance with claim 20 wherein the master node is further configured to selectively generate and include a checksum with critical display messages addressed to the display.

24. A system in accordance with claim 12 in a CT imaging system.

25. A system in accordance with claim 24 wherein the CT imaging system includes a gantry, and at least some of said push buttons are mounted on the gantry.

26. A system in accordance with claim 25 wherein said wired network comprises a controller area network bus.

27. A system for efficiently and reliably communicating button presses electronically, said system comprising a serial network of one or more push button nodes each having at least one push button, and a master node, said system configured to:

periodically generate status messages indicative of a state of the at least one push button at each of the push button nodes;

communicate the status messages to the master node via the wired network;

determine, at the master node, the state of the push buttons at each of the push button nodes from the communicated status messages;

trigger a response of the master node, in accordance with the statuses of the push buttons determined from the communicated status messages;

generate, at each of the push button nodes, a checksum value included in the status message generated at the push button node; and validate the checksum values at the master node to confirm that the master node is receiving valid status messages.

28. A system for efficiently and reliably communicating button presses electronically, said system comprising a serial network of one or more push button nodes each having at least one push button, and a master node, said system configured to:

periodically generate status messages indicative of a state of the at least one push button at each of the push button nodes;

communicate the status messages to the master node via the wired network;

determine, at the master node, the state of the push buttons at each of the push button nodes from the communicated status messages;

trigger a response of the master node, in accordance with the statuses of the push buttons determined from the communicated status messages;

generate, when a push button is pressed, a signal unique to the pressed push button and a signal representing a logical combination of states of all of the push buttons of a posh button node on which the pressed push button is located; and perform a redundancy check on the pressed push button using the signal representing the logical combination of states, at the push button node on which the pressed push button is located.

29. A system in accordance with claim 28 wherein said system being configured to generate a signal representing a logical combination of states of all of the push buttons of a push button node on which the pressed push button is located comprises said system being configured to logically OR a signal for the push button being pressed with signals of all of the other buttons of the push button node on which the pressed push button is located.

30. A system for efficiently and reliably communicating button presses electronically, said system comprising a serial network of one or more push button nodes each having at least one push button, and a master node hard-wired to a critical button of a push button node, said system configured to:

periodically generate status messages indicative of a state of the at least one push button at each of the push button nodes;

communicate the status messages to the master node via the wired network;

determine, at the master node, the state of the push buttons at each of the push button nodes from the communicated status messages;

trigger a response of the master node, in accordance with the statuses of the push buttons determined from the communicated status messages;

immediately communicate a signal indicative of the at least one critical button being pressed separately from the generated status messages; and immediately trigger a response of the master node in accordance with the immediately communicated signal;

said system further configured such that the immediate communication and immediate triggering occurs within a time less than a period of the periodically generated status messages.

\* \* \* \* \*

UNITED STATES PATENT AND TRADEMARK OFFICE
CERTIFICATE OF CORRECTION

PATENT NO. : 6,751,688 B1 Page 1 of 1
APPLICATION NO. : 09/506106
DATED : June 15, 2004
INVENTOR(S) : El-Demerdash et al.

It is certified that error appears in the above-identified patent and that said Letters Patent is hereby corrected as shown below:

In Claim 1, column 5, line 64, delete "One" and insert therefor -- one --.

In Claim 4, column 6, line 19, after "ports" delete -- corresponding --.

In Claim 7, column 6, line 37, delete "comprising" and insert therefor -- comprises --.

In Claim 12, column 8, line 9, delete "states" and insert therefor -- status --.

In Claim 28, column 9, line 39, delete "posh" and insert therefor -- push --.

Signed and Sealed this

Twenty-sixth Day of June, 2007

JON W. DUDAS
*Director of the United States Patent and Trademark Office*